United States Patent
Goodfellow et al.

(10) Patent No.: US 9,526,633 B2
(45) Date of Patent: Dec. 27, 2016

(54) FEMORAL EXTENSION PROSTHETIC COMPONENT AND TIBIAL SHELF PROSTHETIC COMPONENT FOR UNICONDYLAR MENISCAL BEARING KNEE PROSTHESIS AND PROSTHESIS INCLUDING SUCH A COMPONENT

(75) Inventors: John William Goodfellow, Oxfordshire (GB); Colin Hunsley, legal representative, Hants (GB); John O'Connor, Oxford (GB); Chris Alexander Dodd, Oxford (GB); David Wycliffe Murray, Oxford (GB)

(73) Assignees: Biomet UK Limited, Brigend South Glamorgan (GB); John O'Connor, Oxford (GB); Christopher Dodd, Oxford (GB); David Wycliffe Murray, Oxford (GB); Estate of John William Goodfellow, Oxford (GB)

( * ) Notice: Subject to any disclaimer, the term of this patent is extended or adjusted under 35 U.S.C. 154(b) by 203 days.

(21) Appl. No.: 13/821,720

(22) PCT Filed: Sep. 8, 2011

(86) PCT No.: PCT/GB2011/051681
§ 371 (c)(1),
(2), (4) Date: Jun. 18, 2013

(87) PCT Pub. No.: WO2012/032350
PCT Pub. Date: Mar. 15, 2012

(65) Prior Publication Data
US 2013/0317619 A1    Nov. 28, 2013

(30) Foreign Application Priority Data
Sep. 10, 2010 (GB) .................................. 1015087.8

(51) Int. Cl.
A61F 2/38    (2006.01)
A61F 2/46    (2006.01)
A61F 2/30    (2006.01)

(52) U.S. Cl.
CPC ............... *A61F 2/461* (2013.01); *A61F 2/389* (2013.01); *A61F 2/3859* (2013.01);
(Continued)

(58) Field of Classification Search
CPC  A61F 2/3868; A61F 2/389; A61F 2002/3895; A61F 2/38; A61F 2/3836; A61F 2/3854; A61F 2/3886
See application file for complete search history.

(56) References Cited

U.S. PATENT DOCUMENTS 5,336,266 A    8/1994  Caspari et al.
5,358,525 A    10/1994 Fox et al.
(Continued)

FOREIGN PATENT DOCUMENTS

EP    0442330 A2    8/1991
EP    1 584 309 A1   10/2005
(Continued)

OTHER PUBLICATIONS

Notification of Transmittal of the International Search Report and the Written Opinion of the International Searching Authority dated Mar. 20, 2012 in connection with International Patent Application No. PCT/GB2011/051681.
(Continued)

*Primary Examiner* — Marcia Watkins
(74) *Attorney, Agent, or Firm* — Schwegman Lundberg & Woessner, P.A.

(57) ABSTRACT

A femoral extension prosthetic component for use in a unicondylar meniscal bearing unicompartmental knee replacement is described. The femoral component comprises
(Continued)

a securing element and a bearing surface, the securing element adapted to abut and be connected to a distal end of a femur bone, and the bearing surface adapted to abut a meniscal bearing. The femoral component includes an entrapment portion adapted to extend beyond the meniscal bearing. Tibial components and meniscal bearings are also described, as well as methods of using such components.

12 Claims, 4 Drawing Sheets

(52) U.S. Cl.
CPC .. *A61F 2/3868* (2013.01); *A61F 2002/30224* (2013.01); *A61F 2002/30245* (2013.01); *A61F 2002/30403* (2013.01); *A61F 2002/30662* (2013.01); *A61F 2002/30934* (2013.01); *A61F 2002/3895* (2013.01)

(56) References Cited

U.S. PATENT DOCUMENTS

| | | | |
|---|---|---|---|
| 5,871,542 A * | 2/1999 | Goodfellow | A61F 2/3868 623/20.16 |
| 6,004,351 A | 12/1999 | Tomita et al. | |
| 2006/0085078 A1* | 4/2006 | Steffensmeier | 623/20.29 |
| 2008/0243260 A1* | 10/2008 | Lee et al. | 623/20.33 |
| 2008/0243263 A1* | 10/2008 | Lee et al. | 623/20.33 |
| 2009/0043395 A1 | 2/2009 | Hotokebuchi et al. | |

FOREIGN PATENT DOCUMENTS

| | | |
|---|---|---|
| EP | 1693026 A1 | 8/2006 |
| FR | 2788964 A1 | 8/2000 |
| FR | 2832626 A1 | 5/2003 |
| GB | 2 291 355 A | 1/1996 |
| GB | 2 312 377 A | 10/1997 |
| JP | 10155824 A | 6/1998 |
| WO | WO 95/14444 A1 | 6/1995 |
| WO | WO 03/094782 A2 | 11/2003 |
| WO | WO-03094782 A2 | 11/2003 |
| WO | WO 2011/001175 A1 | 1/2011 |
| WO | WO 2011/110865 A2 | 9/2011 |

OTHER PUBLICATIONS

Search Report dated Nov. 17, 2010 in connection with United Kingdom Patent Application No. GB1015087.8.
Search Report dated Oct. 27, 2011 in connection with United Kingdom Patent Application No. GB1015087.8.
Search Report dated Oct. 26, 2011 in connection with United Kingdom Patent Application No. GB1015087.8.
"Chinese Application Serial No. 201180049812.X, Office Action mailed Aug. 11, 2015", (W/ English Translation), 11 pgs.
"Australian Application Serial No. 2011300537, First Examination Report mailed Mar. 17, 2014", 4 pgs.
"Chinese Application Serial No. 201180049812.X, Office Action mailed Jan. 26, 2015", (W/ English Translation), 9 pgs.
"Chinese Application Serial No. 201180049812.X, Office Action mailed Mar. 15, 2016", (W/ English Translation), 6 pgs.
"Chinese Application Serial No. 201180049812.X, Response filed May 26, 2015 to Office Action mailed Jan. 26, 2015", (W/ English Translation of Claims), 9 pgs.
"European Application Serial No. 11779837.1, Intention to grant mailed Mar. 4, 2016", 80 pgs.
"European Application Serial No. 11779837.1, Response filed Dec. 2, 2013 to Communication pursuant to Rules 161(1) and 162 EPC mailed May 29, 2013", 42 pgs.
"International Application Serial No. PCT/GB2011/051681, International Preliminary Report on Patentability mailed Mar. 21, 2013", 14 pgs.
"International Application Serial No. PCT/GB2011/051681, International Search Report mailed Mar. 20, 2012", 7 pgs.
"International Application Serial No. PCT/GB2011/051681, Written Opinion mailed Mar. 20, 2012", 12 pgs.

* cited by examiner

FEMORAL EXTENSION PROSTHETIC COMPONENT AND TIBIAL SHELF PROSTHETIC COMPONENT FOR UNICONDYLAR MENISCAL BEARING KNEE PROSTHESIS AND PROSTHESIS INCLUDING SUCH A COMPONENT

CROSS-REFERENCE TO RELATED APPLICATION(S)

The present application claims priority under 35 U.S.C. §365 to International Patent Application No. PCT/GB2011/051681 filed Sep. 8, 2011. International Patent Application No. PCT/GB2011/051681 claims priority under 35 U.S.C. §365 and/or 35 U.S.C. §119(a) to United Kingdom Patent Application No. 1015087.8 filed Sep. 10, 2010 which are incorporated herein by reference into the present disclosure as if fully set forth herein.

This invention relates to a tibial shelf component for use in unicompartmental, unicondylar, meniscal bearing knee replacements. It also relates to a combination of a tibial component and meniscal bearing for use in such unicompartmental knee replacements. It also relates to a femoral prosthetic component for use in unicompartmental, unicondylar, meniscal bearing knee replacement. It also relates to a method of performing knee arthroplasty.

BACKGROUND OF THE INVENTION

The knee comprises three inter-dependent joints in three separate compartments, all surrounded by a fibrous capsule covered by the skin. The medial tibio-femoral joint involves contact between the thigh bone (the femur) and the leg bone (the tibia) on the inside of the lower limb. The lateral tibio-femoral joint involves contact between the femur and the tibia on the outside of the lower limb. The patello-femoral joint involves contact between the femur and the knee cap (the patella) on the front of the lower limb.

The front of the lower (distal) end of the femur comprises an anticlastic flanged groove, convex in the sagittal plane, transversely concave, providing a track for the patella. The back of the distal femur divides into two separate near-spherical convex condyles making contact with the tibia. The upper surface of the tibia is like a plateau which is slightly dished on the medial side for contact with the medial femoral condyle forming the medial tibio-femoral joint and slightly convex on the lateral side for contact with the lateral femoral condyle forming the lateral tibio-femoral joint with a protrusion (the tibial eminence) running from front to back between the joints.

The articulating surfaces in each joint are covered with thin layers of a tough protective layer called cartilage, and are lubricated by synovial fluid secreted from a membrane on the inner surface of the fibrous capsule surrounding the knee. The surfaces of the tibio-femoral joints are further separated by the menisci, semi-circular semi-lunar collagen bundles oriented circumferentially. Each bundle is securely attached at each end to the tibia. The menisci form closely-fitting mobile sockets for the femoral condyles bringing the dissimilar surfaces of the femur and tibia into closer conformity.

The bones are held together actively by muscles with their tendons which span the joints and passively by ligaments and the joint capsule. The ligaments comprise bundles of collagen fibres running mainly longitudinally. The collateral ligaments arise on the external surfaces of the medial and lateral condyles. The medial collateral ligament inserts into the external medial surface of the proximal tibia. The lateral collateral ligament inserts into the proximal surface of the fibula. The medial collateral ligament is a much larger and stiffer structure than the lateral collateral ligament. The cruciate ligaments arise from the internal surfaces of the femoral condyles and insert into the tibial eminence.

The ligaments and the bones together form a mechanism which controls a complex pattern of movement of the bones on each other. In the unloaded state, flexion of the knee to 130° about a transverse axis is accompanied by approximately 25°rotation about the axis of the tibia (axial rotation) and approximately 5° about an anteroposterior axis (abduction-adduction). These movements are accommodated by mainly anteroposterior translations of the tibio-femoral contact areas so that the bones roll as well as slide on each other and the patella slides over the anterior femur.

Under load, the ligaments stretch and the articular surfaces indent, significantly modifying the relationship between flexion, axial rotation and abduction-adduction and between flexion and contact area translations. Movements at the knee are therefore load and activity dependent.

Damage to the articular surfaces or to the ligaments changes the patterns of movement of the bones on each other and the response of the joint to load. Osteoarthritis follows from failure of the cartilage in one or other of the three joints, leading to bone-on-bone contact and the onset of pain. Frequently, osteoarthritis first manifests itself in the medial compartment, while the ligaments remain intact. The disease can remain confined to the medial compartment until the anterior cruciate ligament fails and the disease then spreads to the other two compartments. No drug treatment has been found which reverses these processes.

Total knee replacement is the most common surgical treatment for osteoarthritis, involving replacement of the articular surfaces of all three compartments and sacrifice of some of the ligaments. Partial knee replacement involves replacement of the articular surfaces in only one compartment, leaving intact the surfaces of the other two compartments and all of the ligaments. Partial knee replacement can act prophylactically, reducing the rate of development of the disease in the other compartments. Partial knee replacement is surgically more demanding and is not always used when it is indicated.

To implant the prosthetic components of a knee replacement, sufficient sections of bone have to be removed from the surfaces of the tibia and the femur. The component parts of the prosthesis are then fitted accurately replacing the material removed by the surgeon. Care has to be taken not to overstuff the joint, leading to pain and failure of the components and, in the case of a partial knee replacement, degeneration of the preserved compartments.

Mobile bearing arthroplasty uses metal components fixed to the tibia and the femur with an intervening plastic bearing, an analogue of the natural meniscus, interposed between. The metal components are fixed to the bones so as to leave a constant gap between them when the knee is flexed and extended. The surgeon then selects the most appropriate thickness of bearing to fill the gap. The bearing is pushed between the metal components against the resistance of stretching ligaments. The bearing snaps into position once its thick section has passed through the thinnest section of the gap between the fixed components. A complication of mobile bearing arthroplasty is dislocation of the bearing. Dislocation rarely occurs after medial partial knee replacement but is the main complication of lateral arthroplasty. The surgeon naturally seeks to use the thickest possible bearing to avoid dislocation. However, if too thick a bearing is selected, there is a risk of overstuffing the joint, which can lead to pain and failure of the components and, in the case of a partial knee replacement, degeneration of the preserved compartments.

The difference between the maximum and minimum thickness of a mobile bearing is a measure of the entrapment of the bearing when it is held in place between the fixed metal components by the ligaments and a measure of the ligament stretch needed to implant or dislocate the bearing in use. A spherically convex tibial component (the domed tibial), similar in shape to the natural lateral tibial plateau, and a bi-concave meniscal bearing were developed to increase entrapment and to reduce the incidence of bearing dislocation after lateral arthroplasty. Nonetheless, lateral bearing dislocation continues to be a problem.

Complete dislocation can occur along the anteroposterior axis of the knee replacement. This can happen either in the anterior direction, as the reverse of the process of implantation, or in the posterior direction. If the patient distracts the joint i.e. by applying appropriate varus or valgus load to the limb, the bearing may be free to move through the enlarged minimum gap and escapes from the embrace of the femoral and tibial components which will then come into contact.

It is more likely to occur if the bearing is tipped at an angle so that it slides out of the gap along the femoral component.

The amount of distraction of the gap between the femoral component and the domed tibial component used in lateral arthroplasty required to cause dislocation can be expressed as follows:

For complete dislocation along tibia, the distraction required is:

$$D_t = \sqrt{x_1^2 + (t_1 + t + R_2)^2} - (R_2 + t)$$

For complete dislocation along the femur, the distraction required is:

$$D_f = \sqrt{x_2^2 + (t_2 + t + R_1)^2} - (R_1 + t)$$

where
$R_1$ is the radius of the femoral component
$R_2$ is the radius of the tibial component
$x_1$ is the length of the posterior portion of the meniscal bearing at upper interface
$x_2$ is the length of the posterior portion of the meniscal bearing at lower interface
$t$ is the minimum thickness of the meniscal bearing
$t_1 = R_1 - \sqrt{R_1^2 - x_1^2}$ is the depth of the upper concavity
$t_2 = R_2 - \sqrt{R_2^2 - x_2^2}$ is the depth of the lower concavity It is also possible for complete dislocation to occur in the lateral direction (towards the outside of the knee). Partial dislocation can occur in the medial direction (towards the inside of the knee) when the bearing moves medially and above the free end of the medial wall of the tibial component before becoming trapped between the fixed components. Partial medial dislocation and complete lateral dislocation continue to be a problem in lateral arthroplasty. Dislocation can also occur in a medial arthroplasty.

We have found it useful herein to define the directions 'inner' and 'outer' when applied to a knee. As used herein, the term 'inner' means central to the knee. Thus the side of a femoral or tibial component which is intended for location closest to the centre of the knee is the 'inner' side. In a lateral arthroscopy, the inner side is the medial side. In a medial arthroscopy, the inner side is the lateral side. Conversely, the term 'outer' is used herein to mean towards the outside of the knee (along a medial-lateral axis). Thus the side of a femoral or tibial component which is intended for location away from the centre of the knee is the 'outer' side. In a lateral arthroscopy, the outer side is the lateral side. In a medial arthroscopy, the outer side is the medial side.

SUMMARY OF THE INVENTION

Several aspects of the invention involve methods of reducing the gap between the inner edges of the femoral and tibial components to reduce the risk of partial dislocation.

According to a first aspect of the invention, we provide a femoral extension prosthetic component for use in a unicondylar meniscal bearing unicompartmental knee replacement, the femoral component comprising a securing element and a bearing surface, the securing element adapted to abut and be connected to a distal end of a femur bone, the bearing surface adapted to abut a meniscal bearing, the femoral component including an entrapment portion adapted to extend beyond the meniscal bearing.

This is advantageous as the entrapment portion increases the entrapment of the meniscal bearing by extending beyond its side wall. In particular, the entrapment portion is arranged such that it reduces the size of the gap between the femoral component and an inner wall of a tibial component of a knee prosthesis. This reduces the chance of the meniscal bearing escaping through the gap therebetween and therefore reduces the chance of medial dislocation in a lateral arthroscopy (or medial dislocation in a medial arthroscopy). The entrapment portion increases the width of the femoral component such that it can be wider than the bearing on the inner or outer side. This is advantageous as the bearing is held more securely. Preferably, the entrapment portion reduces the gap to a size less than the thickness of the meniscal bearing to prevent the meniscal bearing from sliding through.

Preferably, the entrapment portion extends inwardly beyond the meniscal bearing. Preferably, the entrapment portion extends outwardly beyond the meniscal bearing. This is advantageous as, when in use, the entrapment portion extends over the edge or rim of the bearing thereby holding it in place.

Preferably the entrapment portion extends inwardly such that in use it extends beyond the meniscal bearing and the femoral component includes a second entrapment portion extending outwardly such that in use it extends beyond the meniscal bearing. The use of two entrapment portions securely retains the meniscal bearing in use.

Preferably the bearing surface of the femoral component is convex and is adapted to abut a concave bearing surface of the meniscal bearing, the entrapment portion being arranged such that the bearing surface is continued over the entrapment portion. This is advantageous as the entrapment portion retains the bearing while maintaining a smooth continuous surface over which the bearing can move.

The bearing surface of the femoral component and entrapment portion may be arranged such that the apex of the bearing surface is off-centre.

Alternatively the entrapment portion may comprise a projection or flange that extends from an inner or outer side of the femoral component adjacent the bearing surface of the femoral component. Thus, the flange does not continue the convex bearing surface but provides a discontinuous surface to aid in retention of the bearing. This projection on the inner radius of the femoral component is advantageous as it can act to retain the meniscal bearing.

Preferably the entrapment portion projection projects in a distal direction from the femoral component. Preferably, the entrapment portion projection is arranged to project distally to a position substantially level with apex of the convex bearing surface of the femoral component.

Preferably, the projection comprises a hooked flange secured by a longitudinal side to the femoral component adjacent to the bearing surface. Preferably, the projection is constructed and arranged such that it forms a concave region with the bearing surface. The concave region can therefore receive a rim of the bearing.

Preferably the entrapment portion is arranged to project substantially 5 mm mediolaterally beyond the meniscal bearing, in use.

The femoral extension component may be adapted to be used with a tibial component having an inner wall (e.g. a medial wall in a lateral component) and possibly also an outer (e.g. lateral) wall extending from the perimeter of the bearing surface over a portion of the outer side. The femoral entrapment portion may also be adapted to extend outwardly beyond the outer side of the meniscal bearing to reduce the gap between the outer tibial wall and the femoral component. This reduces the chance of the meniscal bearing escaping through the gap therebetween and therefore reduces the chance of lateral dislocation in a lateral arthroscopy, or medial dislocation in a medial arthroscopy.

According to a second aspect of the invention, we provide a tibial shelf prosthetic component for use in a unicondylar meniscal bearing unicompartmental knee replacement, the tibial component comprising a shelf having a connection surface and a bearing surface, the connection surface adapted to abut and be connected to a proximal end of a tibia bone, the bearing surface adapted to abut a meniscal bearing, the tibial shelf including an inner wall extending from the perimeter of the bearing surface over a portion of the inner side, and wherein the tibial shelf also includes an outer wall extending from the perimeter of the bearing surface over a portion of the outer side.

This is advantageous as the inner wall is adapted to retain the meniscal bearing on the tibial shelf when it moves in the inward direction and the outer wall is adapted to retain the meniscal bearing on the tibial shelf when it moves in the outward direction. It also restricts the freedom of the surgeon to place the meniscal bearing too far in the outward direction. This arrangement reduces the risk of medial dislocation and lateral dislocation.

Preferably, the inner wall has an outwardly facing side adjacent to the tibial bearing surface, wherein the outwardly facing side is inclined to an axis of the tibial component. Preferably, the outer wall has an inwardly facing side of the outer wall adjacent to the tibial bearing surface, wherein the inwardly facing side is inclined to an axis of the tibial component.

The tibial component may include an extension at the free end of the inner wall, or at the free end of the outer wall, or at the free ends of both the inner wall and outer wall. The extension may be flexible. The extension may be inclined in an inward direction or an outward direction with respect to the inner wall or outward wall respectively. The extension at the free end of the inner wall may be adapted to be attached to the portion of bone inwardly adjacent to the inner wall and may include a securing element to effect the connection.

The tibial component may include an outwardly extending flange on the outer side of the inner wall, or an inwardly extending flange on the inner side of an outer wall, or both, the flange or flanges adapted to be received in a groove or grooves on the meniscal bearing that are complementary to the flange or flanges.

According to a third aspect of the invention, we provide a tibial shelf prosthetic component for use in a unicondylar meniscal bearing unicompartmental knee replacement, the tibial component comprising a shelf having a connection surface and a bearing surface, the connection surface adapted to abut and be connected to a proximal end of a tibia bone, the bearing surface adapted to abut a bearing element, the tibial shelf including an inner wall extending from the perimeter of the bearing surface over a portion of the inner side, the inner surface of the inner wall adapted to abut a portion of bone, wherein the tibial component includes an extension portion located adjacent a free end of the inner wall and inward therefrom.

This is advantageous as the extension portion extends the inner wall, which effectively increases the total width of the tibial component. This way, in the event of dislocation over the inner wall, the bearing element will be encouraged back down to its correct position on the bearing surface of the tibial component. Also, the extension portion is less likely to come into contact with the femoral component due to its location relative to the wall.

Preferably, the tibial shelf includes an outer wall extending from the perimeter of the bearing surface over a portion of the outer side, wherein the tibial component includes a second extension portion located adjacent a free end of the outer wall and outward therefrom. The outer extension portion can prevent outward dislocation and may be present independently of the inner wall.

The extension portion may be separate from the remainder of the tibial component and may be adapted to be secured to the tibia bone adjacent to and inwards of the free end of the inner wall.

Alternatively the extension portion may be continuous with the inner wall. The extension portion may be adapted to be attached both to the inner wall and to the portion of bone inwards of the inner wall. This is advantageous as the tibial component is easier to install.

Preferably the inner wall comprises a base part that extends from the bearing surface and the extension portion extends from the base part, wherein the extension portion is inclined with respect to the base part. The base part may extend from the bearing surface substantially perpendicular to the plane of the shelf. The extension portion may extend from a free end of the base part, opposite where the base part meets the bearing surface. In particular, the extension portion may be inclined inwardly (i.e. towards the centre of the knee) with respect to the base part at an angle between 10° and 80°. The angle may be between 30° and 60°, or it may be substantially 45°.

Preferably the extension portion is of the same material as the remainder of the wall, although it may be of plastics material. This is advantageous as the plastics material can be selected to be sufficiently rigid to contain the bearing element upon partial dislocation, while being sufficiently flexible to move out of the way of the femoral extension and, should some of the material be sheared or filed off, not to cause serious complications.

Preferably the height of the extension portion is greater than 1 mm. Preferably the height of the extension portion is less than 4 mm. Preferably the height of the extension portion is between 2 mm and 3 mm.

Preferably the extension portion is arched along its length, in the anterior-posterior direction. This provides a sufficient degree of entrapment without unduly restricting movement of the knee prosthesis in use.

Preferably the extension portion extends inwardly (i.e. towards the centre of the knee). Further, the extension portion may have an outwardly facing surface that is inclined to the outwardly facing surface of the remainder of the inner wall. This is advantageous as extending the tibial extension inwardly effectively increases the total width of the tibial component. This way, in the event of dislocation over the inner wall, the bearing element would be encouraged back down to its correct position on the bearing surface of the tibial component. Also, an extension portion of this form is less likely to come into contact with the femoral component. The outer extension portion may have the same features but a mirror image thereof.

According to a fourth aspect of the invention, we provide a tibial shelf prosthetic component for use in a unicondylar meniscal bearing unicompartmental knee replacement, the tibial component comprising a shelf having a connection surface and a bearing surface, the connection surface adapted to abut and be connected to a proximal end of a tibia bone, the bearing surface adapted to abut a bearing element, the tibial shelf including an inner wall extending from the perimeter of the bearing surface over a portion of the inner side, the inner wall having at least a flexible free end.

This is advantageous as the height of the inner wall can be increased because the wall has a flexible free end, which will flex on coming into contact with other parts of the knee prosthesis or bone. If the tibial shelf and femoral extension were of metal (or other rigid material), increasing the height of the inner wall could result in metal on metal contact and metal particles being produced (or other friction-produced debris). With a flexible inner wall, the chance of metal particles being produced is reduced as the wall will flex out of the way and any particles will be of less damaging flexible material. Therefore, the inner wall can be arranged at a height that will significantly reduce the chance of dislocation of the bearing element into the intercondylar notch.

Preferably, the tibial shelf includes an outer wall extending from the perimeter of the bearing surface over a portion of the outer side, the outer wall having at least a flexible free end. This is advantageous as the chance of dislocation in an outward direction can also be reduced. The outer wall with the flexible end may be present independently of the inner wall with flexible end.

Preferably the height of the inner wall and/or outer wall is greater than 6 mm. Preferably the height of the inner and/or outer wall is less than 10 mm. Preferably the height of the inner and/or outer wall is between 7 mm and 9 mm.

Preferably the inner wall comprises a base part proximate to the shelf and an extension part above the base part, the extension part being of a more flexible material than the base part. Thus, the extension part forms the flexible free end of the inner wall.

Preferably the extension part of the inner wall is of plastics material. This is advantageous as the plastics material can be selected to be sufficiently rigid to contain the bearing element, while being sufficiently flexible to move out of the way of the femoral extension and, should some of the material be sheared or filed off, not to cause serious complications. The inner and/or outer wall may be of plastics and the flexible free end may be of more flexible plastics.

Preferably the inner wall is arched along its length, in the anterior-posterior direction. This provides a sufficient degree of entrapment without unduly restricting movement of the knee prosthesis in use.

Preferably the extension part of the inner wall is offset inwardly from the base part of the inner wall. This will significantly reduce the chance of the femoral component or the bearing element contacting the extension part of the inner wall.

Preferably the extension part of the inner wall is arranged to be offset so that the bearing element does not contact the extension part in general use. Thus, contact with the extension part is limited to times when dislocation could occur. Preferably the offset of the extension part is determined according to the inclination of the bearing when the bearing is both substantially contacting the bearing surface of the tibial component and contacting the base part of the medial wall. For a convex bearing surface, the inclination from the vertical α of the bearing when the bearing is both substantially contacting the bearing surface of the tibial component and contacting the base part of the inner wall may be calculated using the formula $$y - x \cos \alpha - (h + x \sin \alpha + \sqrt{R^2 - y^2}) \tan \alpha = 0$$

where
y is the distance from the central eminence of the dome to the outwardly facing side of the inner wall,
x is the half-width of the meniscal bearing,
h is the height of the inner wall from the inner edge of the bearing surface and
R is the radius of the convex bearing surface.

Preferably this offset will be at least 0.4 mm.

The tibial component may include an inclined outwardly facing side of the inner wall or a outer wall extending from the bearing surface over a portion of the outer side.

The extension part of the inner wall may be inclined inwardly (i.e. towards the centre of the knee). This is advantageous as this will effectively increase the width of the tibial component thereby reducing the chance of dislocation in an inward direction. The extension part may be inclined at substantially 45° to the base part.

According to a fifth aspect of the invention, we provide a tibial shelf prosthetic component for use in a unicondylar meniscal bearing unicompartmental knee replacement, the tibial component comprising a shelf having a connection surface and a convex bearing surface, the connection surface adapted to abut and be connected to a proximal end of a tibia bone, the convex bearing surface adapted to abut a concave face of a meniscal bearing, the tibial shelf including an inner wall extending from the perimeter of the bearing surface over a portion of the inner side, the inner wall having an outwardly facing side adjacent to the bearing surface, wherein the outwardly facing side is inclined to an axis of the tibial component.

This is advantageous as the inclined surface can be inclined such that it bears against a side wall of the meniscal bearing. This is thought to reduce the chance of inward dislocation. This is perhaps because when the outwardly facing side of the inner wall is parallel to the axis of the tibial component, the bearing element will slide over the convex bearing surface until its side wall abuts the distal end of the inner wall. The free end of the inner wall provides little resistance to continued movement of the bearing, leading to dislocation. An inclined outwardly facing side can be arranged such that the side wall of the bearing substantially makes contact with the whole inclined side rather than just the distal end. This increased area of contact will increase the resistance to movement of the bearing up the wall. Furthermore, the wider distribution of force will result in less wear on the bearing.

Preferably, the tibial shelf includes an outer wall extending axially from the perimeter of the bearing surface over a portion of the lateral side. Preferably, the inwardly facing side of the outer wall is inclined to the axis of the tibial component. Thus, the tibial component includes a wall to resist outward dislocation as well as inward dislocation.

Preferably, the inclination of the outwardly facing side of the inner wall is chosen such that the inwardly facing side is parallel to a side wall of the meniscal bearing, which abuts the inner wall, in use.

For a convex bearing surface, the inclination from the vertical $\alpha$ of the outwardly facing side of the inner wall may be calculated using the formula $$y-x \cos \alpha - (h+x \sin \alpha + \sqrt{R^2-y^2})\tan \alpha = 0$$

where
y is the distance from the central eminence of the dome to the outwardly facing side of the inner wall,
x is the half-width of the bearing,
h is the height of the inner wall from the inner edge of the bearing surface and
R is the radius of the convex bearing surface.

Preferably, the tibial shelf prosthetic component is adapted for use with a meniscal bearing comprising a first concave bearing surface adapted to bear against a femoral prosthetic component, and a second concave bearing surface opposed to the first concave bearing surface and adapted to bear against the bearing surface of the tibial component, the first and second bearing surfaces being separated by a side wall, wherein the angle formed between the outwardly facing side of the inner wall (of the tibial component) and the convex bearing surface is substantially the same as the angle formed between the side wall and the second concave bearing surface of the meniscal bearing. The shelf and the bearing thus have complementary surfaces which interact to prevent dislocation.

The tibial component may include an outwardly extending flange on the outer side of the inner wall, or an inwardly extending flange on the inner side of an outer wall, or both, the flange or flanges adapted to be received in a groove or grooves in the meniscal bearing that are complementary to the flange or flanges.

The tibial component may include an extension at the free end of the inner wall, or at the free end of an outer wall, or at the free ends of both the inner wall and an outer wall. The extension may be flexible. The extension may be angled in a n inner direction or an outer direction for the inner wall or an outer wall respectively. The extension at the free end of the inner wall may be attached to the portion of bone inwardly adjacent to the inner wall.

According to a sixth aspect of the invention, we provide a combination of a tibial shelf component and a meniscal bearing for use in a unicondylar unicompartmental meniscal bearing knee replacement, the tibial component having a shelf which has a connection surface and a bearing surface, the connection surface adapted to abut and be connected to a proximal end of a tibia bone, the bearing surface adapted to, in use, abut the meniscal bearing, the tibial shelf including an inner wall extending from the perimeter of the bearing surface over a portion of the inner side of the tibial component, wherein the inner wall includes an outwardly extending flange on its outer side and the meniscal bearing includes a groove complementary to the flange, the flange adapted to be received in the groove in use.

This is advantageous as the flange can engage in the recess of the bearing to reduce the chance of medial dislocation of the knee prosthesis. The flange engages the bearing element such that it prevents it lifting from the bearing surface of the tibial shelf.

Preferably, the tibial shelf includes an outer wall extending from the perimeter of the bearing surface over a portion of the outer side of the tibial component, wherein the outer wall includes an inwardly extending flange on its outer side and the meniscal bearing includes a groove complementary to the flange, the flange adapted to be received in the groove in use.

Preferably, the bearing element comprises a first concave bearing surface adapted to bear against a femoral prosthetic component, and a second concave bearing surface opposed to the first concave bearing surface and adapted to bear against the bearing surface of the tibial component, the first and second bearing surfaces being separated by a side wall, wherein the groove is formed in a portion of the side wall.

Preferably, the groove comprises an arcuate track that substantially follows the curve of the second concave bearing surface.

Preferably, the inwardly facing side of the outer wall is inclined to the axis of the tibial component. The inner wall may have an outwardly facing side adjacent to the tibial bearing surface, wherein the outwardly facing side is inclined to an axis of the tibial component. An outer wall may have an inwardly facing side adjacent to the tibial bearing surface, wherein the inwardly facing side is inclined to an axis of the tibial component.

The tibial component may include an extension at the free end of the inner wall, or at the free end of an outer wall, or at the free ends of both the inner wall and an outer wall. The extension may be flexible. The extension may be angled in an inward direction or an outward direction for the inner wall or an outer wall respectively. The extension at the free end of the inner wall may be attached to the portion of bone inwardly adjacent to the inner wall.

According to an seventh aspect of the invention, we provide a tibial shelf prosthetic component for use in a unicondylar meniscal bearing unicompartmental knee replacement, the tibial component comprising a shelf having a connection surface and a bearing surface, the connection surface adapted to abut and to be connected to a proximal end of a tibia bone, the bearing surface adapted to abut a meniscal bearing, the tibial shelf including an inner wall extending from the perimeter of the bearing surface over a portion of the inner side, wherein the bearing surface is curved in the anterior-posterior direction only; or the bearing surface is curved in the medial-lateral direction only; or the bearing surface has a first function of curvature in the anterior-posterior direction and a second function of curvature in the medial-lateral direction.

This is advantageous as the barrel shaped surface or ruled surface can act to reliably retain a meniscal bearing against dislocation. Further, when the bearing surface is curved in both the anterior-posterior direction and medial-lateral direction, the functions of curvature can be selected to ensure a balance of security against dislocation and freedom of movement of the joint.

When the bearing surface is curved in both the anterior-posterior direction and the medial-lateral direction, the first function of curvature may be different to the second function of curvature.

Preferably, the tibial shelf includes an outer wall extending from the perimeter of the bearing surface over a portion of the outer side.

According to an eighth aspect of the invention, we provide a meniscal bearing prosthetic component for use in a unicondylar meniscal bearing unicompartmental knee replacement, the meniscal bearing comprising a first concave bearing surface adapted to bear against a femoral prosthetic component, and a second concave bearing surface opposed to the first concave bearing surface and adapted to bear against a tibial prosthetic component, the first and second bearing surfaces being separated by a side wall, wherein the side wall is thicker on the outer side than on the inner side.

This is advantageous as the shape of the meniscal bearing acts to reduce the chance of medial dislocation. To dislocate medially, the lateral side of the meniscal bearing must move between the femoral prosthetic component and the tibial prosthetic component. By making the lateral side of the bearing thicker, the gap between the femoral prosthetic component and the tibial prosthetic component must be larger for dislocation to occur. Thus, the chance of medial dislocation is reduced. The meniscal bearing of the eighth aspect may be used in combination with the femoral component of the first aspect of the invention.

Preferably the thickness of the outer side is 1 mm larger than the inner side.

According to a ninth aspect of the invention, we provide a method of performing knee arthroplasty using a tibial component of the second, third, fourth, fifth or seventh aspects of the invention with a femoral component and a meniscal bearing, or the combination of a tibial component and meniscal bearing of the sixth aspect of the invention with a femoral component, or a femoral component of the first aspect of the invention with a tibial component and a meniscal bearing, or a meniscal bearing of the sixth aspect of the invention with a femoral component and a tibial component comprising;

preparing a femur bone to receive the femoral component;
preparing a tibia bone to receive the tibial component;
securing the femoral component to the femur bone;
securing the tibial component to the tibia bone; and
inserting the bearing between the femoral component and the tibial component.

It will be appreciated that the components of the aspects of the invention may be used with one another to form a kit of parts comprising a tibial component, a femoral extension component and a meniscal bearing for use in a unicondylar meniscal bearing unicompartmental knee replacement.

In the aspects of the invention described above, where the component is for use in a lateral unicompartmental knee replacement, the inner wall may be a medial wall, and the outer wall (if present) may be a lateral wall. Where the component is for use in a medial unicompartmental knee replacement, the inner wall may be a lateral wall, and the outer wall (if present) may be a medial wall.

It will be appreciated that each of the components defined in the above aspects of the invention could include the features of the other aspects of the invention.

DETAILED DESCRIPTION OF THE DRAWINGS

There now follows by way of example only a detailed description of the present invention with reference to the accompanying drawings in which.

DETAILED DESCRIPTION

Figure 1:
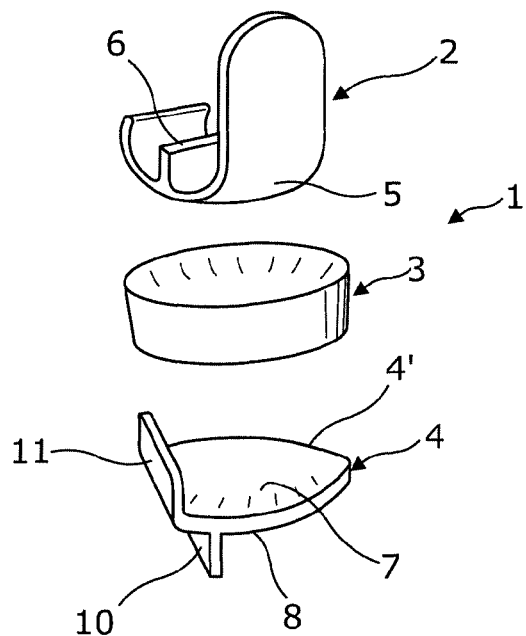
FIG. 1 shows a known unicompartmental unicondylar meniscal bearing knee prosthesis.

FIG. 1 shows a known knee prosthesis 1 comprising a femoral component, or femoral extension, 2, a meniscal bearing 3 and a tibial component 4. The femoral component 2 is adapted to be connected to a femoral condyle of the femur bone and comprises a bearing surface 5 and securing element 6. The meniscal bearing comprises a bi-concave disc of plastics. The tibial component 4 is adapted to be connected to the tibial plateau of the tibia bone. The tibial component 4 has a tibial shelf 4' which comprises a shelf having a convex bearing surface 7 on one side and a connection surface 8 on an opposed side. The connection surface 8 includes a securing element 10. The bearing surface 7 includes an inner wall 11 that extends axially from the periphery thereof. The prosthesis 1 shown in FIG. 1 is adapted to be secured to the lateral side of the left knee, and so in the example shown the inner wall is a medial wall.

Figure 2A:
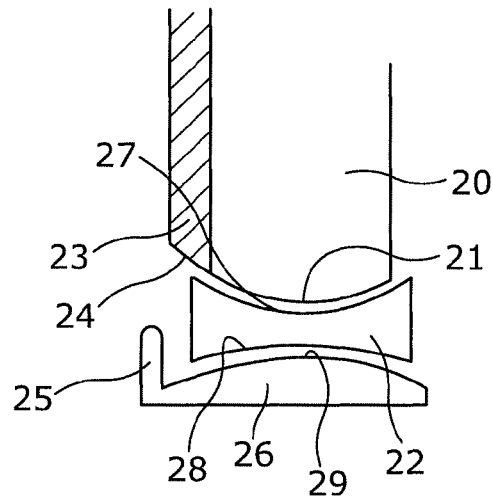
FIG. 2a shows a cross-sectional front view of an embodiment of a knee prosthesis having a femoral component in accordance with the first aspect of the invention.

FIG. 2a shows an anteroposterior view of a knee prosthesis that includes a femoral extension prosthetic component 20 comprising a securing element (not visible) and a bearing surface 21. The securing element is adapted to abut and be connected to a distal end of a femur bone. The bearing surface 21 is adapted to abut a meniscal bearing 22. The femoral component 20 includes an inwardly extending entrapment portion 23 (shaded region) adapted to extend inwardly beyond the meniscal bearing 22. In this example the entrapment portion extends medially, and so the entrapment portion 23 decreases the size of the gap between the femoral component and medial wall of the tibial component. The entrapment portion 23 increases the width of the femoral component 20 by at least 10%. The entrapment portion 23 projects substantially 5 mm medially beyond the meniscal bearing when the knee is in the extended position as shown in the Figures.

The entrapment portion 23 includes an entrapment bearing surface 24 which forms a continuation of the bearing surface 21. Thus, the convex curve of the bearing surface 21 is continued by the entrapment bearing surface 24. The entrapment bearing surface 24 acts to prevent the meniscal bearing 22 lifting from the tibial prosthetic component 26 and dislocating over the medial wall 25. The presence of the entrapment portion 23 causes the bearing surface 21, including the bearing surface 24, to be asymmetric and, in particular, the apex of the combined bearing surface is off-centre towards the lateral side. If a lateral entrapment portion is present, the apex may be off-centre towards the medial side. If both a medial and lateral entrapment portion is present the apex may be central.

The entrapment portion 23 is sized and arranged to be aligned with the medial wall 25 of the tibial component 26 when in use and the knee is extended.

The meniscal bearing 22 comprises a bi-concave disc having a first concave bearing surface 27 adapted to bear against the femoral component 20, and a second concave bearing surface 28 opposed to the first concave bearing surface 27 and adapted to bear against a convex bearing surface 29 of the tibial shelf component 26.

Figure 2B:
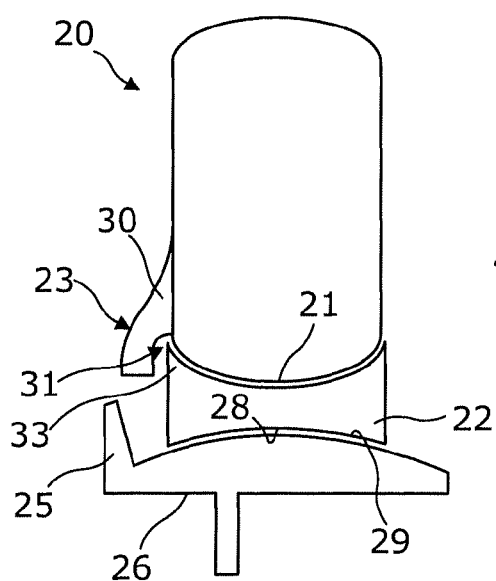
FIG. 2b shows a cross-sectional front view of a further embodiment of a knee prosthesis having a femoral component in accordance with the first aspect of the invention.

FIG. 2b shows an anteroposterior view of a further embodiment of a knee prosthesis that includes the femoral prosthetic component 20. The same reference numerals have been used for the same parts, as present in FIG. 2a. In this embodiment, the entrapment portion 23 comprises a projection 30 that extends from the femoral component adjacent the bearing surface 21 on the inner, in this case medial, side. The projection 30 extends from the lower medial edge of the femoral component and is arranged to extend towards the medial wall 25 of a tibial component 26 when in use. The lower edge of the projection 30 may be arranged to extend to the same level as the apex of the bearing surface 21. The projection 30 is secured by a longitudinal side to the femoral component 20 adjacent to the bearing surface 21 and first extends medially and then distally. The projection 30 defines a concave region 31 at the point it joins the bearing surface 21 between it and the bearing surface 21. The concave region 31 retains the meniscal bearing 22 when it moves medially and prevents it lifting over the medial wall 25 of the tibial component 26.

In particular, the concave region is arranged to receive a rim 33 of the meniscal bearing 22 (i.e. the edge formed between the side wall and the concave bearing surface arranged to abut the femoral component).

Figure 3:
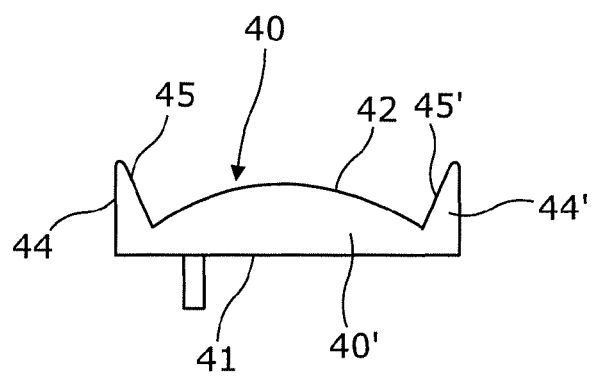
FIG. 3 shows a cross-sectional front view of an embodiment of a tibial component of a knee prosthesis in accordance with the second aspect of the invention.

FIG. 3 shows an anteroposterior view of a tibial shelf prosthetic component 40 comprising a shelf 40' having a connection surface 41 and a convex bearing surface 42. The connection surface 41 is adapted to abut and be connected to a proximal end of a tibia bone. The convex bearing surface 42 is adapted to abut a concave face of a meniscal bearing. The tibial shelf 40' includes an inner wall, in this case medial wall 44, extending from the perimeter of the bearing surface over a portion of the inner, medial, side. The medial wall 44 has a laterally facing inclined side 45 adjacent to the bearing surface 42. The tibial shelf 40' also includes an outer, lateral, wall 44' extending from the convex bearing surface 42 of the lateral peripheral side. The lateral wall 44' is substantially a mirror image of the medial wall 44 and includes a medially facing inclined side 45'. The lateral wall 44' acts to retain the meniscal bearing on the tibial shelf when it moves in the lateral direction. It also inhibits placement of the femoral component and the bearing too far laterally, reducing the risk of medial dislocation.

It will be appreciated that the medial wall 44 and lateral wall 44' need not have inclined sides 45 and 45' and could alternatively extend perpendicular to the connection side 41. Alternatively, one of the medial wall 44 and lateral wall 44' could include an inclined side to receive the side wall of the meniscal bearing.

Figures 4A, 4B:
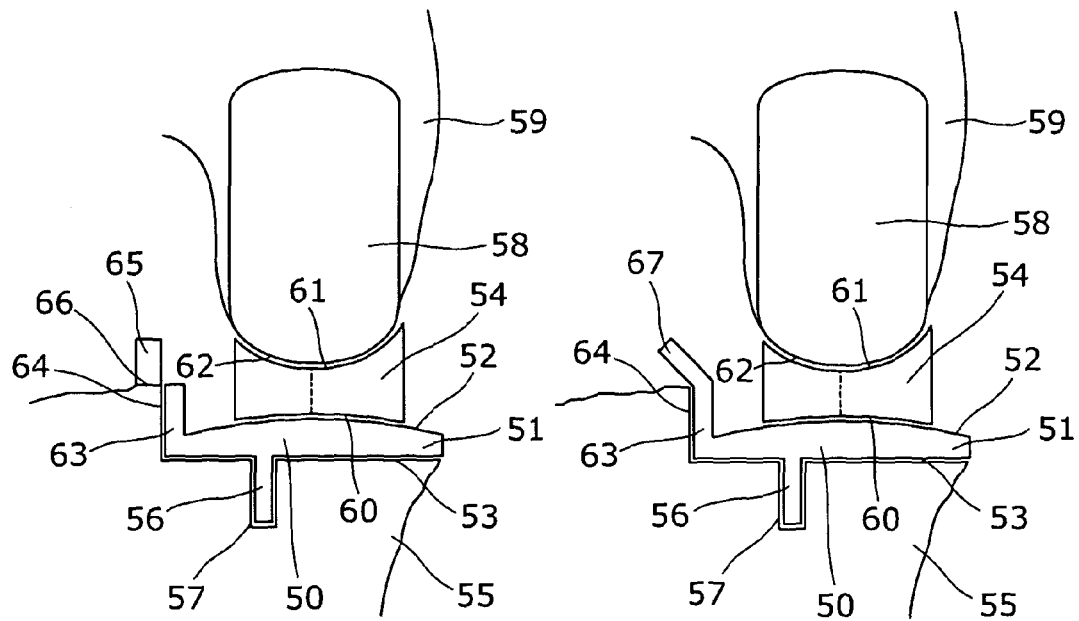
FIG. 4a shows a side view of an embodiment of a tibial component of a knee prosthesis in accordance with the third aspect of the invention.
FIG. 4b shows a cross-sectional front view of a further embodiment of a tibial component of a knee prosthesis in accordance with the third aspect of the invention.

FIGS. 4a and 4b show a view of a tibial shelf prosthetic component 50 in a unicondylar meniscal bearing unicompartmental knee replacement. The tibial component 50 comprises a shelf 51 having a bearing surface 52 and an opposed connection surface 53. The bearing surface 52 is adapted to abut a bearing element 54, in use. The connection surface 53 is adapted to be secured to a proximal end of a tibia bone 55. To aid the connection, the connection surface 53 includes a keel 56 that extends into a groove 57 that is made in the tibia bone 55.

The bearing element 54 is arranged to be located between the tibial component 50 and a femoral component 58 in a unicondylar meniscal bearing unicompartmental knee replacement. The femoral component 58 is secured to a femur bone 59. In this embodiment, the bearing element 54 has a concave lower surface 60 and a concave upper surface 61, which engages with a bearing surface 62 of the femoral component 58.

The tibial component 50 includes an inner wall, in this case medial wall 63, extending from the perimeter of the bearing surface 52 over a portion of the inner, medial side. The medial wall 63 is designed to abut the laterally facing surface 64 of the proximal end of the tibial bone 55.

In FIG. 4a, in addition to the tibial component 50, an extension portion 65 is shown. The extension portion 65 is adapted to be secured to a surface 66 of the proximal end of the tibia bone 55 inwardly adjacent (in this case medially adjacent) to the free end of the inner wall (medial wall 63). The extension portion 65 includes a securing part to secure it to the tibia 55. The extension portion 65 is elongate in the anteroposterior direction and includes an arched upper edge. In the embodiment of FIG. 4a, the medial wall 63 and the extension portion 65 form a stepped region to aid in retention of the meniscal bearing against medial dislocation. However, the extension portion 65 may include an inclined laterally facing side (with respect to the medial wall 63), which may extend over the free end of the medial wall 63.

FIG. 4b shows a further embodiment and the same reference numerals have been used. However, in this embodiment the extension portion 67 forms part of the inner (medial) wall 63 rather than solely being secured to the tibia 55. It will be appreciated that the extension portion 67 could be secured to the tibia in addition to forming part of the medial wall 63.

The medial wall 63 extends from the perimeter of the bearing surface 52 of the tibial component 51 over a portion of the medial side. The medial wall includes a base part that extends from the bearing surface in a direction substantially perpendicular to the plane of the tibial component 51. The extension portion 67 extends from the free end of the base part of the medial wall 63. The extension portion 67 extends outwardly in a medial direction. The extension portion 67 is inclined relative to the medial wall 63 (and also to the shelf 51) at an angle of substantially 45°. The extension portion 67 increases the width of the tibial component 50.

Figures 5A, 5B:
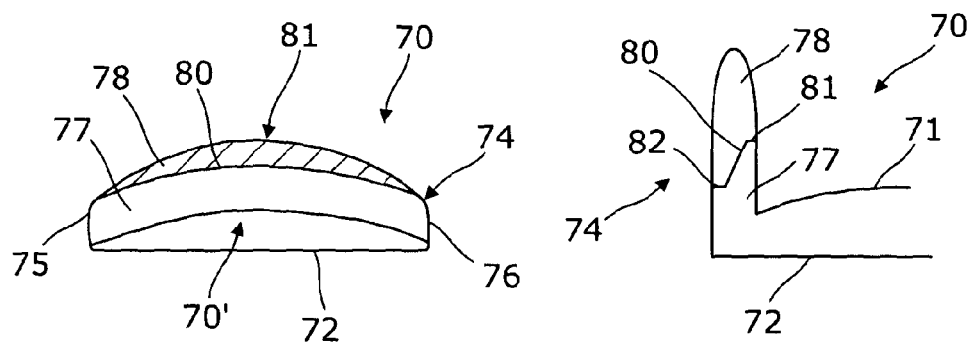
FIG. 5a shows a side view of an embodiment of a tibial component of a knee prosthesis in accordance with the fourth aspect of the invention.
FIG. 5b shows a cross-sectional front view of an embodiment of a tibial component of a knee prosthesis in accordance with the fourth aspect of the invention.

FIG. 5a and FIG. 5b show medial and anteroposterior views of an embodiment of a tibial component 70 in accordance with the fourth aspect of the invention. The tibial component 70 has a tibial shelf 70' which comprises a substantially D-shaped shelf having a convex bearing surface 71 on one side and a connection surface 72 on an opposed side. The connection surface 72 includes a securing element (not shown). The bearing surface 71 includes an inner wall, in this example, medial wall 74, that extends axially from the periphery thereof. The medial wall 74 extends around approximately a third of the perimeter of the bearing surface 71. The medial wall 74 is also arched over its longitudinal direction. Thus, it rises from the bearing surface 71 at a first end 75, rises to a maximum height and then decreases in height to a second end 76.

The medial wall 74 comprises a base part 77 (proximate to the tibial shelf 70) and an extension part 78. The base part 77 extends from the bearing surface 71 and is of the same material as the remainder of the tibial shelf 70', which may be a cobalt chromium alloy. The maximum height of the base part 77 is typically 5 mm. The extension part 78 extends from a free end 80 of the base part 77. The extension part 78 increases the height of the medial wall 74 a further 2-3 mm at its centre point. The extension part 78 is of a flexible material, such as plastics (typically polyethylene). In particular, the extension part 78 is of a more flexible material than the base part 77 and is sufficiently flexible not to cause damage to the intercondylar notch or surrounding bone when installed in a knee. The extension part 78 increases the height of the medial wall 74 to reduce the chance of the bearing element 3 moving such that a partial medial dislocation can occur. The extension part 78 may form up to half of the total height of the medial wall 74. The extension part being of plastics is advantageous as if the extension part 78 was of metal, it could contact the metal femoral part 2 which could lead to the production of metal particles. The metal particles could cause major damage inside the knee.

The free end 80 of the base part 77 is stepped such that an inner edge 81, adjacent to the bearing surface 71, is higher than an outer edge 82, adjacent to the periphery of the tibial shelf 70. The extension part 78 is compression moulded onto the free end 80. The extension part 78 is of substantially the same length as the base part 77. The extension part 78 is arched along its length and thus it rises from the base part 77 adjacent to the first end 75, where it is of nominal height. It reaches a maximum height above the base part 77 at a centre point 81 along its length and then decreases in height to a point adjacent to the second end 76, where it is of nominal height.

In use, the tibial component 70 is secured to the tibia, the femoral component 8 is secured to the femur and a bearing is inserted therebetween. The bearing is biconcave and is adapted to slide between the femoral component 2 and tibial component 70. The increased height of the medial wall 74 provided by the extension part 78 helps reduce the chance of partial medial dislocation of the bearing element and obviates the risk of grains of metal debris being produced by metal components rubbing together within the knee.

Figure 6A:
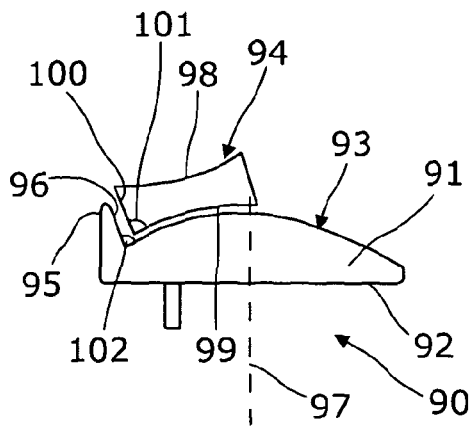
FIG. 6a shows a front view of an embodiment of a tibial component of a knee prosthesis in accordance with the fifth aspect of the invention.

FIG. 6a shows an anteroposterior view of a tibial shelf prosthetic component 90 comprising a shelf 91 having a connection surface 92 and a convex bearing surface 93. The connection surface 92 is adapted to abut and be connected to a proximal end of a tibia bone. The convex bearing surface 93 is adapted to abut a concave face of a meniscal bearing 94. The tibial shelf 91 includes an inner wall, in this case medial wall 95, extending from the perimeter of the bearing surface over a portion of the inner, medial side. The medial wall 95 has a laterally facing side 96 adjacent to the bearing surface 93. The laterally facing side 96 is inclined to an axis 97 of the tibial component. The axis 97 of the tibial component extends perpendicular to the connection surface 92.

The laterally facing side 96 is inclined such that it extends from a medially inward position adjacent to the bearing surface 93 to a medially outward position adjacent to a free end of the medial wall 95. This inclination is selected to improve how the tibial component interacts with a meniscal bearing. The meniscal bearing 94 comprises a bi-concave disc having a first concave bearing surface 98 adapted to bear against a femoral extension (not shown in FIG. 6), and a second concave bearing surface 99 opposed to the first concave bearing surface 98 and adapted to bear against the convex bearing surface 93 of the tibial shelf 91. The second concave bearing surface 99 is complementary to the convex bearing surface 93. The first and second bearing surfaces 98, 99 are separated by a side wall 100.

In FIG. 6a, the meniscal bearing 94 is shown adjacent to the medial wall 95 bearing against the medial side of the bearing surface 93. It will be appreciated that in the Figure, the components are shown with a slight gap between them for clarity. The inclination of the laterally facing side 96 substantially matches the inclination of the side wall 100 of the meniscal bearing 94 when it is bearing against the convex bearing surface 93 and is adjacent to the medial wall 95. In particular, the angle 101 formed between the side wall 100 and the second concave bearing surface 99 is substantially the same as the angle 102 formed between the inclined laterally facing side 96 and the convex bearing surface 93.

Accordingly, contact between the tibial component 90 and the meniscal bearing 94 occurs between the laterally facing side 96 of the medial wall 95 and the side wall 100, of the meniscal bearing 94, rather than just between the free end of the medial wall and the side wall 100. This increased area of contact will increase the resistance to movement of the meniscal bearing 94 up the medial wall 95. Furthermore, the wider distribution of force will help prevent wear on the side wall 100 of the meniscal bearing 94.

Figure 6B:
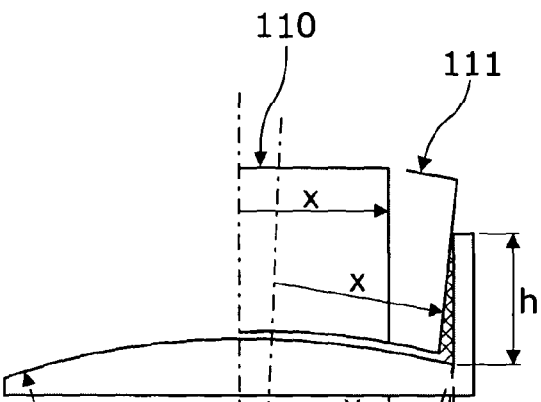
FIG. 6b shows a diagram that illustrates a calculation of the inclination of the bearing when the bearing is both substantially contacting the bearing surface of the tibial component and contacting the medial wall.

FIG. 6b shows the determination of an appropriate angle 102 formed between the inclined laterally facing side 96 and the convex bearing surface 93. FIG. 6b shows a diagram which labels the dimensions of a tibial component having an inclined medial/lateral wall. The diagram shows the meniscal bearing in a first position 110 centrally, symmetrically located on the bearing surface. It also shows the bearing in a second position 111 on the medial side abutting the medial wall. For a convex bearing surface, the inclination from the vertical α of the bearing when the meniscal bearing is both substantially contacting the bearing surface of the tibial component and contacting the base part of the medial wall may be calculated using the formula $$y - x\cos\alpha - (h + x\sin\alpha + \sqrt{R^2 - y^2})\tan\alpha = 0$$

where y is the distance from the central eminence of the domed bearing surface to the laterally facing side of the medial wall, x is the half-width of the meniscal bearing, h is the height of the medial wall from the medial edge of the bearing surface and R is the radius of the convex bearing surface.

Figure 7A:
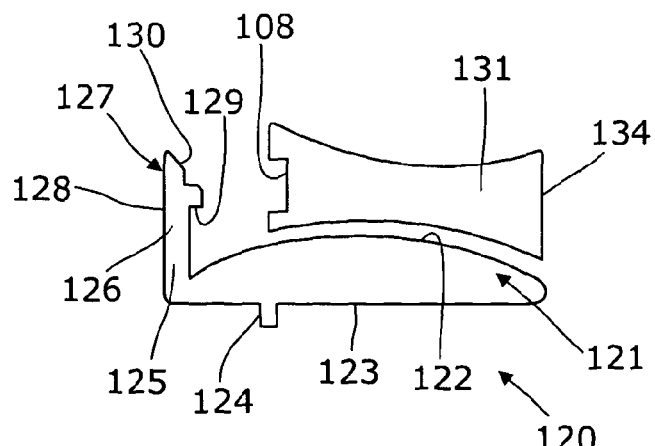
FIG. 7a shows a cross-sectional front view of an embodiment of a tibial component of a knee prosthesis in accordance with the sixth aspect of the invention.

FIG. 7a shows an anteroposterior view of an embodiment of a tibial component 120 and a meniscal bearing in accordance with the sixth aspect of the invention. The tibial component 120 comprises a tibial shelf 121 having a substantially D-shaped shelf having a convex bearing surface 122 on one side and a connection surface 123 on an opposed side. The connection surface 123 includes a securing element 124. The bearing surface 122 includes an inner wall, in this case medial wall 125, that extends axially from the periphery thereof. The medial wall 125 extends around approximately a third of the perimeter of the bearing surface 122. The medial wall 125 is also arched over its direction. Thus, it rises from the bearing surface 122 at a first end (not visible), rises to a maximum height and then decreases in height to a second end 126.

The medial wall 125 includes a laterally extending retaining flange 127 that projects from a free end 128 of the medial wall 125 over a portion of its length. The retaining flange 127 comprises a detent portion 129 and an inclined deflection surface 130.

Figure 7B:
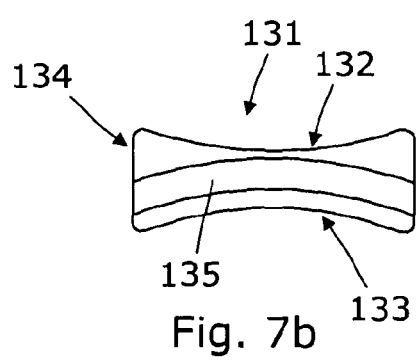
FIG. 7b shows a side view of an embodiment of a meniscal bearing of a knee prosthesis in accordance with the sixth aspect of the invention.

The bearing 131, as shown in FIG. 7b, substantially has the shape of a bi-concave disc. In particular, the bearing 131 comprises a first concave bearing surface 132 and a second concave bearing surface 133 opposed to the first concave bearing surface 132, the bearing surfaces 132 and 133 being separated by a side wall 134. The first concave bearing surface 132 is adapted to bear against the femoral component 2. The second concave bearing surface 133 is adapted to bear against the bearing surface 122 of the tibial shelf 121. A retention groove 135 is formed in a portion of the side wall 134 that is complementary to the retaining flange 127. The retention groove 135 comprises an arcuate track that substantially follows the curve of the second concave bearing surface 133, through the centre of the bearing element 131, as can be seen in the lateral view of the bearing in FIG. 7b.

In use, the tibial component 120 is secured to the tibia, the femoral component 2 is secured to the femur and the bearing element 131 is inserted therebetween. The retention groove 135 of the bearing element 131 is substantially aligned with the retaining flange 127. On movement of the bearing element 131 towards the medial wall 125, the retaining flange 127 enters the retention groove 135. If the bearing element 131 were to lift, such as in the event of a partial medial dislocation, the detent portion 128 will engage the retention groove 135 and prevent it lifting further from the bearing surface 122. Thus, the detent acts to prevent partial medial dislocation of the bearing element 128. The position of the retention groove 135 is advantageous as it is located below the upper surface of the meniscal bearing. This ensures that the retaining flange 127 does not interfere with a femoral component of the knee prosthesis when the components are in use. The deflection surface 130 acts to direct a bearing that has lifted past the retaining flange 127 back onto the bearing surface 122.

Figures 8A, 8B:
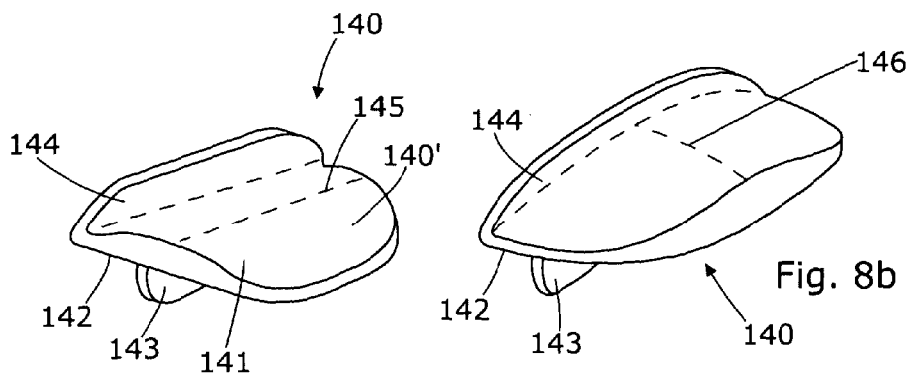
FIG. 8a shows a first embodiment of the tibial component of the seventh aspect of the invention.
FIG. 8b shows a second embodiment of the tibial component of the seventh aspect of the invention.

FIG. 8a shows a first embodiment of the seventh aspect of the invention. The tibial component 140 has a tibial shelf 140' which is substantially D-shaped in plan view, having a bearing surface 141 on one side and a connection surface 142 on an opposed side. The connection surface 142 includes a securing element 143. The bearing surface 141 includes an inner wall, in this case medial wall 144, that extends axially from the periphery thereof. The medial wall 144 extends around approximately a third of the perimeter of the bearing surface 141. In this embodiment, the bearing surface 141 is curved in the medial-lateral direction only and thus appears barrel shaped, with the axis of the barrel extending in the anterior-posterior direction. The peak of the ridge formed by the curved surface thus extends in the anterior-posterior direction and is shown by dashed line 145.

The bearing surface 141 is substantially flat in the anterior-posterior direction. In this embodiment, the peak of the ridge 145 extends through the centre of the bearing surface 141, but it could be offset to the medial or lateral sides.

FIG. 8b shows a second embodiment of the seventh aspect of the invention. The same reference numerals have been used for the same features as those shown in FIG. 8a. This embodiment differs from that of FIG. 8a as the bearing surface 141 is not curved in medial-lateral direction. Instead, it is curved in the anterior-posterior direction only. Thus, the bearing surface 141 is barrel shaped but with the axis of the barrel extending in the medial-lateral direction. The peak of the ridge formed by the curved surface thus extends in the medial-lateral direction and is shown by dashed line 146. The bearing surface 141 is substantially flat in the medial-lateral direction. In this embodiment, the peak of the ridge 146 extends through the centre of the bearing surface 141, but it could be offset to the anterior or posterior sides.

Figure 8C:
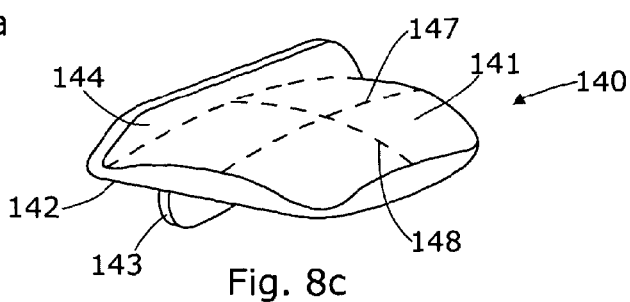
FIG. 8c shows a third embodiment of the tibial component of the seventh aspect of the invention.

FIG. 8c shows a third embodiment of the tibial component 140 of the seventh aspect of the invention. Once again the same reference numerals have been used for the same features as those shown in FIGS. 8a and 8b. In this embodiment, the bearing surface 141 has a first function of curvature in the anterior-posterior direction and a second function of curvature in the medial-lateral direction. Thus, the surface may be a quadric surface. The first function of curvature is different to the second function of curvature. It will be appreciated that the functions of curvature could be the same depending on the configuration of the knee replacement components. The ridge 127 of the anterior-posterior curve and the ridge 128 of the medial-lateral curve intersect at the centre of the bearing surface 141. It will be appreciated that the apex of the surface could be offset from the centre of the bearing surface 141.

Figures 9, 10:
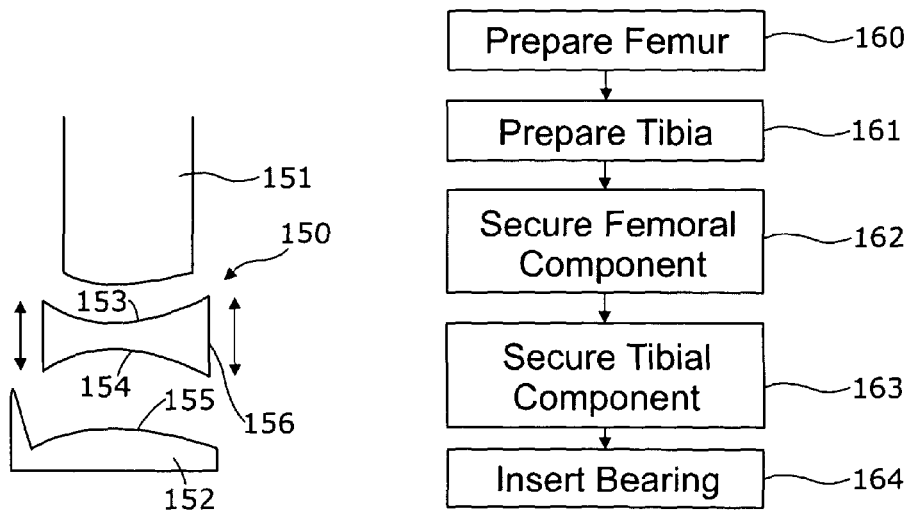
FIG. 9 shows a cross-sectional front view of an embodiment of a tibial component and meniscal bearing in accordance with the eighth aspect of the invention.
FIG. 10 shows a flow chart illustrating the method of surgery of the ninth aspect of the invention.

FIG. 9 shows a diagrammatic anteroposterior view of a meniscal bearing 150 of the eighth aspect of the invention located between a femoral component 151 and a tibial shelf component 152. The meniscal bearing 150 comprises a bi-concave disc having a first concave bearing surface 153 adapted to bear against the femoral extension component 151, and a second concave bearing surface 154 opposed to the first concave bearing surface 153 and adapted to bear against a convex bearing surface 155 of the tibial shelf component 152. The first and second bearing surfaces 153, 154 are separated by a side wall 156. The side wall 156 is thicker on the outer, in this case lateral, side than it is on the inner, in this case medial, side of the meniscal bearing 150. In this embodiment, this difference in thickness is at least 1 mm. The thicker lateral side wall 156 will provide resistance to medial dislocation as the femoral component 151 will have to separate from the tibial component 152 a substantial distance before the thicker side wall 156 can pass between them. This reduces the risk of medial dislocation.

FIG. 10 shows a flow chart of the method of performing knee arthroplasty. Step 160 comprises preparing a femur bone to receive a femoral component. Step 161 comprises preparing a tibia bone to receive the tibial component. Step 162 comprises securing the femoral component to the femur bone. Step 163 comprises securing the tibial component to the tibia bone. Step 164 comprises inserting the bearing between the femoral component and the tibial component. It will be appreciated that the steps can be performed in a different order. For example, step 160 followed by step 162 and then step 161 followed by step 163 or vice versa. If the tibial component of FIG. 4a or FIG. 4b is used, it may be necessary to resect part of the tibia 55 to accommodate the extension portion 65 or 67. Therefore, the tibia 55 may be prepared with a flat or inclined surface 66 complementary to the extension portion 65 or 67 respectively.

It will be appreciated that the use of the terms 'medial' and 'lateral' in describing the components shown in the Figures is by way of example only, and is not intended to limit the invention to the embodiments shown.

The invention claimed is:

1. A tibial shelf prosthetic component for use in a unicondylar meniscal bearing unicompartmental knee replacement, the tibial shelf prosthetic component comprising:
 a tibial shelf having a connection surface and a convex bearing surface, the connection surface adapted to abut and be connected to a proximal end of a tibia bone, the convex bearing surface adapted to abut a first concave face of a meniscal bearing, the tibial shelf including an inner wall extending from a perimeter of the bearing surface over a portion of an inner side, the inner wall having an outwardly facing side adjacent to the bearing surface, wherein the outwardly facing side is inclined to an axis of the tibial shelf which is perpendicular to the connection surface;
 wherein the inclination of the outwardly facing side of the inner wall is chosen such that:
  the outwardly facing side of the inner wall is inclined to a side wall of the meniscal bearing when the meniscal bearing is remote from the outwardly facing side of inner wall; and
  the outwardly facing side of the inner wall is parallel to the side wall of the meniscal bearing when the meniscal bearing abuts the outwardly facing side of the inner wall.

2. The tibial shelf prosthetic component according to claim 1, wherein:
 the tibial shelf includes an outer wall extending from the perimeter of the bearing surface over a portion of an outer side, the outer wall having an inwardly facing side adjacent to the bearing surface; and
 the inwardly facing side is inclined to the axis of the tibial shelf.

3. The tibial shelf prosthetic component according to claim 2, wherein the outer wall includes an extension portion that is located adjacent a free end of the outer wall and outward therefrom.

4. The tibial shelf prosthetic component according to claim 1, wherein:
 the tibial shelf prosthetic component is adapted for use with the meniscal bearing comprising a second concave face adapted to bear against a femoral prosthetic component, the first concave face of the meniscal bearing and the second concave face of the meniscal bearing separated by a side wall.

5. The tibial shelf prosthetic component according to claim 1, wherein the inner wall includes an extension portion that is located adjacent a free end of the inner wall and inward therefrom.

6. The tibial shelf prosthetic component according to claim 1, wherein at least one of the inner wall or an outer wall extending from the perimeter of the bearing surface over a portion of an outer side has a flexible free end.

7. The tibial shelf prosthetic component according to claim 1, wherein the inner wall includes an outwardly extending flange on the outwardly facing side, the flange arranged to engage in a complimentary groove in the meniscal bearing in use.

8. The tibial shelf prosthetic component according to claim 1, wherein the tibial shelf includes an outer wall, and in which the outer wall comprising an inwardly extending flange on an inwardly facing side, the flange arranged to engage in a complimentary groove in the meniscal bearing in use.

9. The tibial shelf prosthetic component according to claim 1, wherein the bearing surface has one of:
 (i) a curvature in a medial-lateral direction only; or
 (ii) a curvature comprising a first function of curvature in an anterior-posterior direction and a second function of curvature in the medial-lateral direction.

10. A combination comprising:
 a tibial shelf prosthetic component and a meniscal bearing for use in a unicondylar meniscal bearing unicompartmental knee replacement;
 wherein the tibial shelf prosthetic component comprises:
  a tibial shelf having a connection surface and a convex bearing surface, the connection surface adapted to abut and be connected to a proximal end of a tibia bone, the tibial shelf including an inner wall extending from a perimeter of the bearing surface over a portion of an inner side, the inner wall having an outwardly facing side adjacent to the bearing surface, wherein the outwardly facing side is inclined to an axis of the tibial shelf prosthetic component which is perpendicular to the connection surface;
 wherein the inclination of the outwardly facing side of the inner wall is chosen such that:
  the outwardly facing side of the inner wall is inclined to a side wall of the meniscal bearing when the meniscal bearing is remote from the outwardly facing side of inner wall; and
  the outwardly facing side of the inner wall is parallel to the side wall of the meniscal bearing when the meniscal bearing abuts the outwardly facing side of the inner wall; and
 wherein the meniscal bearing comprises a first concave bearing surface adapted to bear against a femoral prosthetic component and a second concave bearing surface opposed to the first concave bearing surface and adapted to bear against the convex bearing surface of the tibial shelf, the first and the second concave bearing surfaces being separated by the side wall of the meniscal bearing, wherein the side wall of the meniscal bearing is thicker on an outer side than an inner side.

11. The combination of claim 10, wherein the convex bearing surface of the tibial shelf has one of:
 (i) a curvature in a medial-lateral direction only; or
 (ii) a curvature comprising a first function of curvature in an anterior-posterior direction and a second function of curvature in the medial-lateral direction.

12. A method of performing knee arthroplasty using a tibial component with a femoral component and a meniscal bearing, the method comprising:
 preparing a femur bone to receive the femoral component;
 preparing a tibia bone to receive the tibial component;
 securing the femoral component to the femur bone;
 securing the tibial component to the tibia bone; and
 inserting the meniscal bearing between the femoral component and the tibial component;
 wherein the tibial component comprises a tibial shelf having a connection surface and a convex bearing surface, the connection surface adapted to abut and be connected to a proximal end of the tibia bone, the tibial shelf including an inner wall extending from a perimeter of the bearing surface over a portion of an inner side, the inner wall having an outwardly facing side adjacent to the bearing surface, wherein the outwardly facing side is inclined to an axis of the tibial shelf which is perpendicular to the connection surface;

wherein the inclination of the outwardly facing side of the inner wall is chosen such that:

the outwardly facing side of the inner wall is inclined to a side wall of the meniscal bearing when the meniscal bearing is remote from the outwardly facing side of inner wall; and the outwardly facing side of the inner wall is parallel to the side wall of the meniscal bearing when the meniscal bearing abuts the outwardly facing side of the inner wall; and wherein the meniscal bearing comprises a first concave bearing surface adapted to bear against the femoral component and a second concave bearing surface opposed to the first concave bearing surface and adapted to bear against the convex bearing surface of the tibial shelf, the first and the second concave bearing surfaces being separated by the side wall of the meniscal bearing, wherein the side wall of the meniscal bearing is thicker on an outer side than an inner side.

* * * * *